United States Patent [19]

Matsumiya et al.

[11] Patent Number: 5,225,346
[45] Date of Patent: Jul. 6, 1993

[54] CULTURE BAG

[75] Inventors: Toshiharu Matsumiya, Yamaguchi; Shozo Shiraishi, Kanagawa; Kazuo Sakamoto, Yamaguchi; Shoji Sakakiyama, Yamaguchi; Masahachi Yoshioka, Yamaguchi, all of Japan

[73] Assignee: Sekisui Chemical Co., Ltd., Osaka, Japan

[21] Appl. No.: 723,074

[22] Filed: Jun. 28, 1991

[30] Foreign Application Priority Data

Jun. 29, 1990 [JP] Japan ............................ 2-70275[U]
Jun. 29, 1990 [JP] Japan ............................ 2-70276[U]
Jun. 29, 1990 [JP] Japan ................................ 2-174094

[51] Int. Cl.$^5$ ............................................. C12M 3/00
[52] U.S. Cl. ............................... 435/284; 435/296; 435/313; 435/818; 383/102; 428/35.2; 428/35.4
[58] Field of Search ................................. 435/284–286, 435/296, 311, 313, 315, 316, 818, 2; 383/102, 106; 525/227; 428/35.2, 35.4, 36.6, 36.7; 422/102; 604/408, 410

[56] References Cited

U.S. PATENT DOCUMENTS

| 3,102,082 | 8/1963 | Brewer | 435/301 |
| 3,184,395 | 5/1965 | Brewer | 435/299 |
| 4,135,026 | 1/1979 | Hoyt et al. | 525/61 |
| 4,698,372 | 10/1987 | Moss | 521/149 |
| 4,910,147 | 3/1990 | Bacehowski et al. | 435/284 |
| 4,939,151 | 7/1990 | Bacehowski et al. | 435/284 |
| 4,968,624 | 11/1990 | Bacehowski et al. | 435/284 |

FOREIGN PATENT DOCUMENTS

| 0101028 | 2/1984 | European Pat. Off. . |
| 0148161 | 7/1985 | European Pat. Off. . |
| 2435524 | 4/1980 | France . |
| WO90/03427 | 4/1990 | PCT Int'l Appl. . |

OTHER PUBLICATIONS

Chemical Abstract No. CA113(26):233044j (Aug. 20, 1990).
Chemical Abstract No, CA105(20:173740f (Mar. 31, 1986).

*Primary Examiner*—Michael G. Wityshyn
*Assistant Examiner*—William H. Beisner
*Attorney, Agent, or Firm*—Armstrong, Westerman, Hattori, McLeland & Naughton

[57] ABSTRACT

Disclosed herein is a culture bag which has a culture room formed by fusion-bonding a transparent sheet and at least one opening formed therein, the sheet being made of a resin composition composed of 100 parts by weight of vinyl chloride homopolymer or copolymer and 150–260 parts by weight of ethylene-n-butyl acrylate-carbon monoxide copolymer, and having a gas permeability of 600–3000 ml/m$^2$.24hr.atm to oxygen and a gas permeability of 1000–30,000 ml/m$^2$.24hr.atm to carbon dioxide.

7 Claims, 3 Drawing Sheets

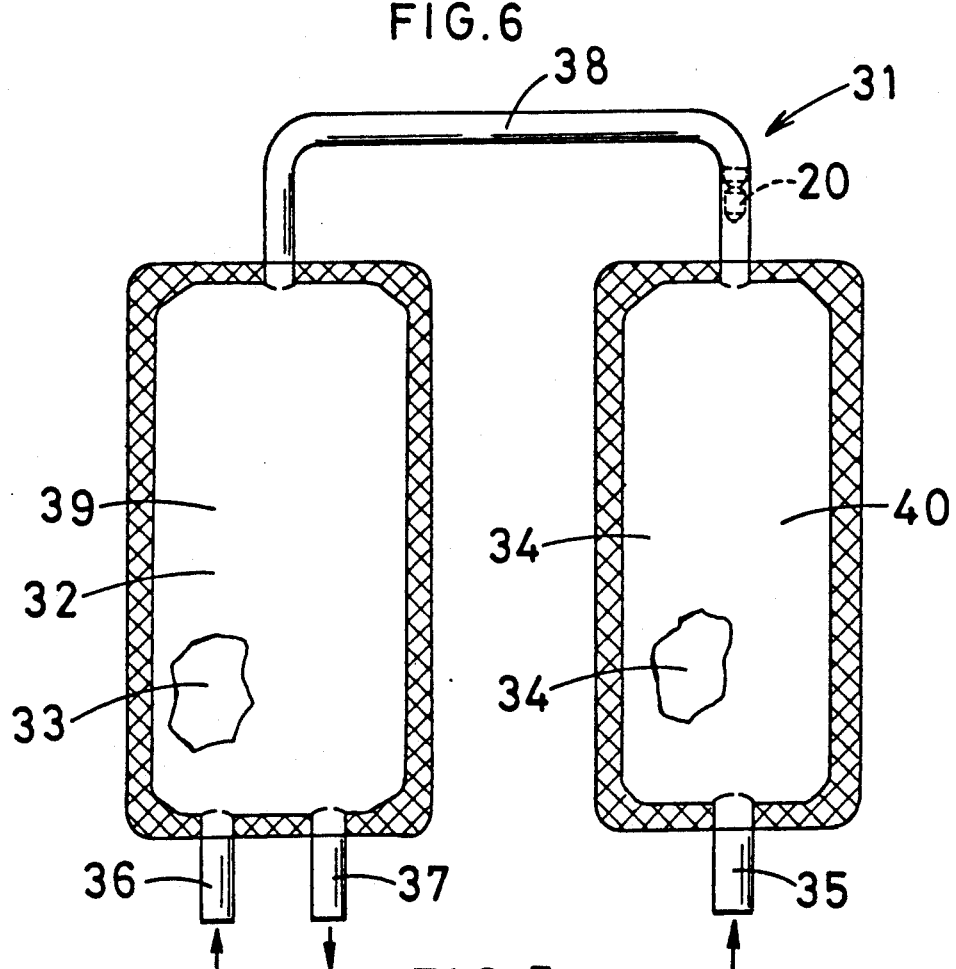
FIG.6
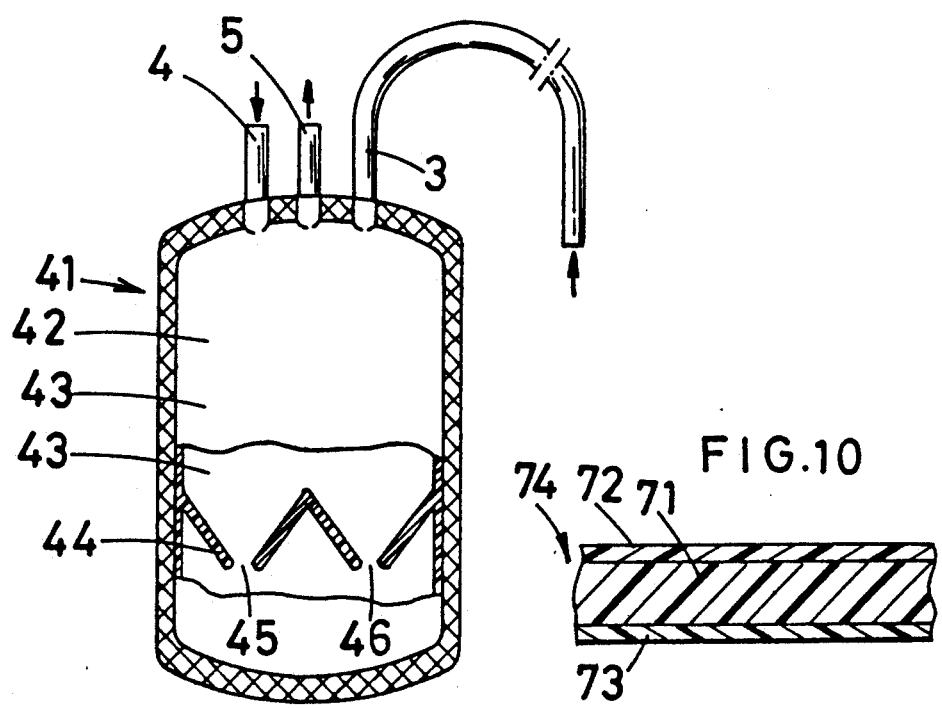
FIG.7
FIG.10

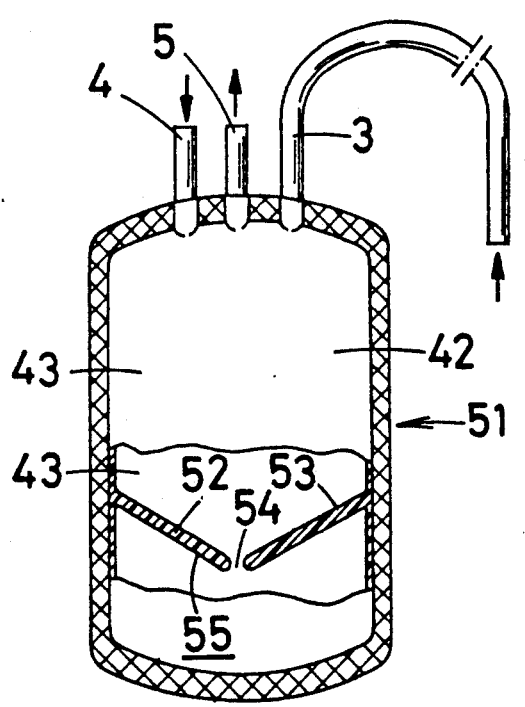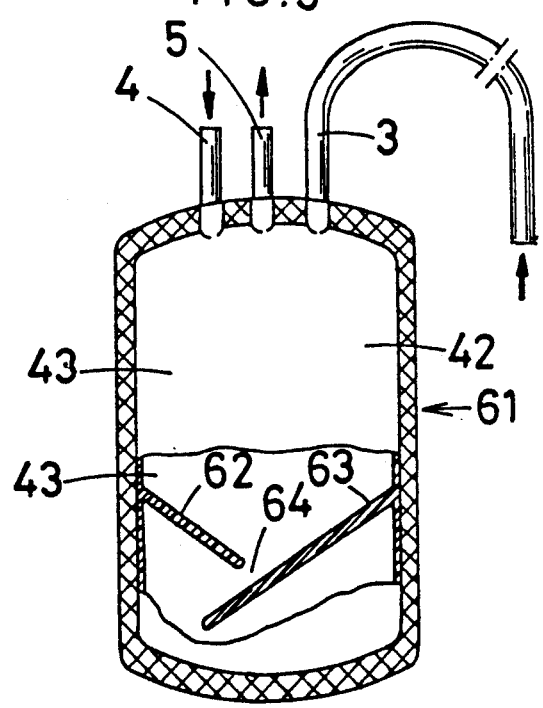

CULTURE BAG

BACKGROUND OF THE INVENTION

1. Field of the Invention

The present invention relates to a culture bag for culturing cells such as animal tissue. More particularly, it is concerned with a culture bag made of plastic sheet having good flexibility, clarity, and gas permeability.

2. Description of the Prior Art

The culture of cells (such as animal tissue) in open-type containers such as Petri dish and flask has a disadvantage that the culture medium is liable to contamination with airborne infectious microbes which enter the incubator when it is opened. To cope with this problem, there have been proposed a variety of closed-type containers as mentioned below.

"Biotechnology Series, Technique of Cell Culture" pp. 137–141, issued by Kodansha Scientific (1985), describes using plastic bags for the culture of wallsticking cells.

Japanese Patent Laid-Open No. 214178/1988 discloses a cell culture container consisting of a bag-like container proper (formed by bonding two flexible plastic sheets to each other) and an inlet tube and an outlet tube each provided with a coupler at its end. According to this disclosure, the container should be made of a different material depending on its use. For aerobic culture, the preferred material includes ethylene-vinyl acetate copolymer, polyethylene, polypropylene, polybutadiene, Teflon ®, and silicone rubber, which have good gas permeability. For anaerobic culture, the preferred material includes polyvinylidene chloride, polyvinyl alcohol, polyethylene terephthalate, and copolymer of acrylonitrile-butadiene rubber grafted with acrylonitrile and methyl methacrylate, which have good gas barrier properties. In addition, these materials may be combined with one another to form a laminate, if necessary.

Japanese Patent Laid-open No. 202378/1988 (U.S. patent Ser. No. 008,213) discloses a technique of culturing specific cells in an airtight container provided with an access tube. According to this disclosure, the airtight container is made of a copolymer film about 0.04–0.23 mm thick, having an oxygen permeability not smaller than about $1.8 \times 10^5$ $\mu m^3$ (STP) per $m^2$.sec.Pa. The copolymer film is one which is formed by lamination or coextrusion from any of (a) ethylene-α-olefin ($C_{4-10}$) copolymer having a density of about 0.91–0.925 g/cm$^3$, (b) ethylene-methacrylic acid copolymer, (c) an ionomer, and (d) ionomer/polyester elastomer and linear low-density polyethylene elastomer.

The containers proposed in the above-mentioned disclosures have a disadvantage in clarity and gas permeability and hence they cannot be used as cell culture bags.

Japanese Patent Publication No. 50063/1980 (U.S. Pat. No 3,780,140) discloses a resin composition from which to produce flexible plastic containers. This resin composition is composed of a copolymer consisting essentially of (a) 40–80 wt. % ethylene, (b) 3–30 wt. % carbon monoxide, and (c) 5–60 wt. % comonomer (preferably vinyl acetate) and polyvinyl chloride or any other polymer in an amount low enough for it to be compatible with said copolymer.

SUMMARY OF THE INVENTION

It is an object of the present invention to provide a culture bag which has an adequate degree of gas permeability to oxygen and carbon dioxide and permits one to freely control the area of gas permeation per unit volume, and which is superior in clarity.

The present invention was completed to achieve the above-mentioned object.

The first aspect of the present invention is embodied in a culture bag which comprises a culture room formed by fusion-bonding a transparent sheet for the culture room (this sheet will be referred to as the "sheet for the culture room" in the specification and claims) and at least one opening formed therein, said sheet being made of a resin composition composed of 100 parts by weight of vinyl chloride homopolymer or copolymer and 150–260 parts by weight of ethylene-n-butyl acrylate-carbon monoxide copolymer, and having a gas permeability of 600–3000 ml/$m^2$.24hr.atm to oxygen and a gas permeability of 1000–30,000 ml/$m^2$.24hr.atm to carbon dioxide.

The second aspect of the present invention is embodied in a culture bag which comprises an integrally formed culture room and medium storage room, and at least one each of cell injection opening and medium discharge opening formed in the culture room and a medium injection opening formed in the medium storage room, with the culture room and medium storage room communicating with each other through a passage, said culture bag being formed by fusion-bonding the peripheries of two sheets for the storage room (this sheet will be referred to as the "sheet for the storage room" in the specification and claims) and one sheet for the culture room in such a manner that the two sheets for the storage room face to each other to form the medium storage room and one of the two sheets for the storage room and the one sheet for the culture room face to each other to form the culture room, said sheet for the storage room being made of a resin composition composed of 100 parts by weight of vinyl chloride homopolymer or copolymer and 30–150 parts by weight of ethylene-vinyl acetate-carbon monoxide copolymer, and having a gas permeability of 100–350 ml/$m^2$.24hr.atm to oxygen and a gas permeability of 200–1000 ml/$m^2$.24hr.atm to carbon dioxide, said sheet for the culture room being defined as above.

The third aspect of the present invention is embodied in a culture bag which comprises a culture room formed by fusion-bonding the sheet for the culture room (defined above) and a medium storage room formed by fusion-bonding the sheet for the storage room (defined above), said two rooms communicating with each other through a passage connected to at least one opening formed in the culture room and at least one opening formed in the medium storage room.

The culture bags defined in the first, second, and third aspects of the present invention may be constructed such that the two sheets constituting the culture room are partially fusion-bonded to form a partition which separates the culture room into upper and lower compartments, said partial fusion-bonding being accomplished in such a manner that at least one unsealed part forms a cell passage and the upper side of at least one of the sealed parts functions as the guide which leads cells to the unsealed part. In addition, the sheet for the culture room constituting the culture bags may be a three-layer laminate sheet, with the outer layers being made of a resin composition composed of 100 parts by weight of vinyl chloride homopolymer or copolymer and 150-260 parts by weight of ethylene-n-butyl acrylate-carbon monoxide copolymer, the core being made of ethylene-n-butyl acrylate-carbon monoxide copolymer.

In the present invention the gas permeability to oxygen and carbon monoxide was measured according to ASTM D1434, the melt flow rate was measured according to ASTM D1238, and the total light transmittance was measured according to JIS K7105.

BRIEF DESCRIPTION OF THE DRAWINGS

FIG. 6 is a partly cutaway plan view showing the culture bag in Example 6.

FIGS. 7 to 9 are partly cutaway plan views showing the culture bags in Example 7.

FIG. 10 is a sectional view showing the sheet for the culture room in Example 10.

DETAILED DESCRIPTION OF THE INVENTION

Figure 1:
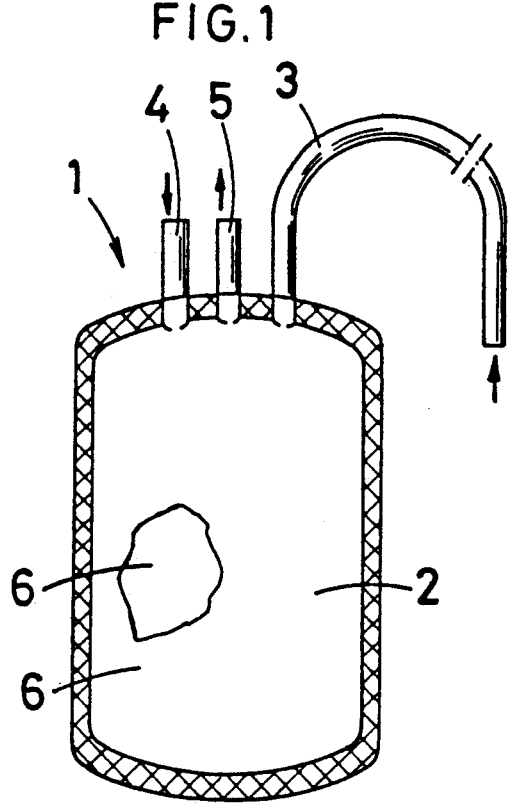
FIG. 1 is a partly cutaway plan view showing the culture bags in Examples 1 to 4.

The culture bag pertaining to the first aspect of the present invention comprises an airtight culture room and at least one opening formed therein, said culture room being formed by fusion-bonding a transparent sheet for the culture room having specific properties.

Oxygen is necessary for cells to grow in a medium and carbon dioxide is necessary for a medium to be in the pH range 7.4-7.6. At a pH higher than 7.8, cell growth does not proceed smoothly. Therefore, it is necessary that the culture bag be made of a material having a good gas permeability to oxygen and carbon dioxide. In addition, the material for culture bags should have flexibility, heat-sealability that ensures airtightness, good clarity that permits the microscopic examination of cell growth, and freedom from plasticizers (such as dioctyl phthalate and diisodecyl phthalate) which are toxic to cells. The sheet for the culture room to meet these requirements is made of a resin composition composed of 100 parts by weight of vinyl chloride homopolymer or copolymer and 150-260 parts by weight, preferably 170-230 parts by weight, of ethylene-n-butyl acrylate-carbon monoxide copolymer. It has a gas permeability of 600-3000 ml/m$^2$.24hr.atm, preferably 800-2600 ml/m$^2$.24hr.atm, to oxygen and a gas permeability of 1000-30,000 ml/m$^2$.24hr.atm, preferably 1500-25,000 ml/m$^2$.24hr.atm, to carbon dioxide. If the amount of ethylene-n-butyl acrylate-carbon monoxide copolymer is less than specified above, the resulting sheet is poor in clarity and flexibility; in the opposite case, the resulting sheet is poor in strength and liable to blocking. The sheet for the culture room should have a total light transmittance of 80-100%.

The vinyl chloride homopolymer or copolymer mentioned above should be one which has an average degree of polymerization of 300-5000, preferably 800-2000, as measured according to JIS K6721. The vinyl chloride copolymer may contain as one or more comonomers α-olefins (such as ethylene and propylene), vinyl esters (such as vinyl acetate and vinyl stearate), vinyl ethers (such as methyl vinyl ether and cetyl vinyl ether), vinyl halides (such as vinyl bromide and vinyl fluoride), unsaturated acids (such as maleic acid, maleic anhydride, and fumaric acid) and esters thereof, and other vinyl and vinylidene compounds than mentioned above (such as styrene, acrylonitrile, and vinylidene chloride). The content of the comonomer should be 1-10 wt. %, preferably 2-8 wt. %. The preferred vinyl chloride copolymer is a vinyl chloride-ethylene copolymer containing 2-8 wt. % ethylene and having an average degree of polymerization of 800-2000.

The ethylene-n-butyl acrylate-carbon monoxide copolymer should be one which is composed of 40-80 wt. %, preferably 60-70 wt. %, ethylene, 15-60 wt. %, preferably 20-35 wt. %, n-butyl acrylate, and 5-30 wt. %, preferably 5-15 wt. %, carbon monoxide. This copolymer may be produced by copolymerization of the comonomers by vigorous stirring at a high temperature (preferably 160°-230° C.) under a high pressure (preferably 24,000-27,000 psi) in a reactor in the presence of a polymerization catalyst such as t-butyl peroxyisobutyrate and azodiisobutyronitrile. If necessary, this copolymer may be further copolymerized with an additional comonomer. This copolymer should have a melt flow rate of 1-500 g/10 min, preferably 5-100 g/10 min.

The resin composition for the sheet for the culture room may be prepared by melt-blending the vinyl chloride homopolymer or copolymer and the ethylene-n-butyl acrylate-carbon monoxide copolymer, together with optional additives including a stabilizer (such as calcium stearate and zinc stearate), a lubricant (such as polyethylene wax and stearic acid), and the like. The blending may be accomplished by using a batchwise mixer (such as roll and mixer) or a continuous mixer (such as twin-screw extruder).

The sheet for the culture room may be produced by extruding the resin composition in pellet form. The sheet should be 0.1-0.5 mm thick, preferably 0.15-0.4 mm thick. With a thickness smaller than 0.1 mm, the culture bag would be broken during filling. With a thickness larger than 0.5 mm, the sheet would be poor in clarity and gas permeability.

The culture room should have at least one opening which is formed preferably at one end thereof. This opening is used to inject and discharge a medium and washing liquid such as saline solution and phosphate buffer saline solution, to inject cells, to recover cultured cells, and to sample cells during culture. This opening is formed by attaching a tube (preferably 3-5 mm in diameter) to the culture room. This tube should preferably be made of the same material as that from which the culture room is made. This tube may be produced by extruding the resin composition in pellet form.

The culture bag of the present invention may be formed from two pieces of the sheet for the culture room cut in approximate rectangle of desired size from the web. The two sheets are placed one over the other, with a tube for the opening held between them at one end thereof, and the peripheries of the sheets are fusion-bonded together with the tube by high-frequency sealing or heat sealing which makes the culture bag completely airtight.

The culture bag of the present invention is used in the following manner. First, the culture bag is sterilized by ethylene oxide. The sterilized culture bag (with or without a sterilized bag holding it) is brought into a clean bench. The culture bag (which constitutes the culture room) is supplied with a culture medium and cells through the opening. The opening is closed with a pinch-cock or a sterilized cap or rubber stopper to keep the culture bag airtight. The culture bag is allowed to stand for the static culture of cells in a desired gas atmosphere. After culture is completed, the culture bag is emptied of the culture medium and cultured cells through the opening. During culture, sampling may be facilitated if the culture room is provided with a sampling tube having a rubber cap inserted therein.

Since the sheet from which the culture bag is made has good gas permeability and clarity, the culture bag mentioned above offers an advantage that it permits the permeation of as much gas as necessary for cell culture and it also permits the content to be observed from outside. Therefore, the culture bag permits the culture in an airtight system and hence prevents the entrance of infectious microbes into the culture medium. In addition, the culture bag can be easily made in any desired shape and size by fusion-bonding. The sheet for the culture room has a good gas permeability which can be controlled as desired by selecting a proper sheet thickness and blending ratio for the resin composition.

The culture bag pertaining to the second aspect of the present invention comprises an integrally formed culture room and medium storage room, and at least one each of cell injection opening and medium discharge opening formed in the culture room and a medium injection opening formed in the medium storage room, with the culture room and medium storage room communicating with each other through a passage, said culture bag being formed by fusion-bonding the peripheries of two sheets for the storage room and one sheet for the culture room in such a manner that the two sheets for the storage room face to each other to form the medium storage room and one of the two sheets for the storage room and the sheet for the culture room face to each other to form the culture room.

This culture bag employs the same sheet for the culture room as used for the culture bag pertaining to the first aspect of the present invention. The medium storage room is formed from the sheet for the storage room which has a low gas permeability so that the medium storage room protects the medium from deterioration by oxidation. In addition, the storage room should be made of a sheet capable of fusion-bonding so that the culture bag is airtight. To meet these requirements, the sheet for the storage room is formed from a resin composition composed of 100 parts by weight of vinyl chloride homopolymer or copolymer and 30–150 parts by weight, preferably 40–120 parts by weight, of ethylene-vinyl acetate-carbon monoxide copolymer, and having a gas permeability of 100–350 ml/m$^2$.24hr.atm to oxygen and a gas permeability of 200–1000 ml/m$^2$.24hr.atm, preferably 200–900 ml/m$^2$.24hr.atm, to carbon dioxide.

The vinyl chloride homopolymer or copolymer from which the sheet for the storage room is made is the same one as that from which the sheet for the culture room is made. The ethylene-vinyl acetate-carbon monoxide copolymer as one component of the above-mentioned resin composition should preferably be one which is produced by copolymerization of 100 parts by weight of ethylene, 10–90 parts by weight of vinyl acetate, and 3–50 parts by weight of carbon monoxide. This copolymer may be produced by copolymerization of the co- monomers by vigorous stirring at a high temperature (preferably 155°–230° C.) under a high pressure (preferably 20,000–35,000 psi) in a reactor in the presence of a polymerization catalyst such as t-butyl peroxyisobutyrate and azodiisobutyronitrile. This copolymer should have a melt flow rate of 0.1–500 g/10 min, preferably 0.5–100 g/10 min.

The sheet for the storage room may be produced in the same manner as the sheet for the culture room. It should be 0.2–0.5 mm thick, preferably 0.3–0.4 mm thick. With a thickness smaller than 0.2 mm, the storage room would burst when it is filled and be poor in gas barrier properties. With a thickness larger than 0.5 mm, the storage room does not permit the smooth discharging of its contents.

The culture room is usually provided with at least one opening for cell injection and at least one opening for medium discharge, which are formed at one end thereof. The storage room is provided with an opening for medium injection. These two rooms communicate with each other through a passage. The openings and a passage may be formed in the same manner as mentioned above. They should be formed from a tube, 3–5 mm in inside diameter, made by extrusion molding of the same material as that of which the rooms are made.

The culture bag pertaining to the second aspect of the present invention may be formed from two pieces of the sheet for the storage room and one piece of the sheet for the culture room, both cut in approximate rectangle of desired size from the web. The three sheets are placed one over the other, with tubes for the openings and the passage held between them at desired positions, in such a manner that the former two sheets face to each other to form the medium storage room and one of the former two sheets and the latter sheet face to each other to form the culture room. The peripheries of the three sheets are fusion-bonded together with the tubes by high-frequency sealing or heat sealing which ensures complete airtightness.

The thus obtained culture bag consists of the culture room and the medium storage room which are integrally formed. It is used in the following manner. First, the medium storage room is filled with a culture medium, with the passage closed. On the occasion of starting the culture, the passage is opened and the medium is transferred from the storage room to the culture room, and cells are injected into the culture room through the opening for cell injection. The culture bag is placed in an incubator of desired gas atmosphere for static culture. Finally, the medium is discharged through the medium discharge opening, and the discharged medium is tested for grown cells. The medium storage room keeps the medium in good conditions, because it is constructed of two sheets of vinyl chloride type resin having good oxygen permeability and carbon dioxide permeability. The culture room permits gas permeation through the outside sheet and also permits the observation of its contents through the outside sheet, which is made of a transparent vinyl chloride type resin having good oxygen permeability and carbon dioxide permeability.

As mentioned above, the culture bag pertaining to the second aspect of the present invention has integrally formed two rooms, one being the medium storage room to store the medium in good conditions, the other being the culture room which permits the permeation of gas necessary for culture and also permits the observation of its contents from outside. Moreover, the two rooms communicate with each other through a passage, so that the medium can be transferred from the medium storage room to the culture room. An advantage of this constitution is that the medium can be injected into the culture room in a very short time without contamination. An additional advantage is that the integrally formed storage room and culture room are easy to handle.

The culture bag pertaining to the third aspect of the present invention is made up of one culture room and one medium storage room, each having at least one opening, which rooms communicate with each other through a passage. The culture room is made of sheets for the culture room, and the medium storage room is made of sheets for the storage room. The sheet for the culture room is the same as that in the case of the culture bag pertaining to the second aspect of the present invention. Also, the sheet for the culture room is the same as that in the case of the culture bag pertaining to the second aspect of the present invention.

According to a preferred embodiment, the culture room is provided with an opening for cell injection and an opening for medium discharge, and the medium storage room is provided with an opening for medium injection. The culture room may be formed from two pieces of the sheet for the culture room cut in approximate rectangle of desired size from the web. The two sheets are placed one over the other, with tubes held between them at desired positions, and the peripheries of the sheets are fusionbonded together with the tubes by high-frequency sealing or heat sealing. The medium storage room may also be formed from two pieces of the sheet for the storage room in the same manner as mentioned above.

The culture bag pertaining to the third aspect of the present invention may be used basically in the same manner as the culture bag pertaining to the second aspect of the present invention.

The above-mentioned three types of culture bags may be produced by an alternative method. For example, the culture room or medium storage room may be formed from a folded sheet in place of two flat sheets. In the case of the first and third types of the culture bag, the culture room may be formed from one piece of the sheet for the culture room and one piece of a sheet which is not originally intended for the culture room. In other words, there is no problem if one of the two sheets constituting the culture room is the sheet for the culture room. The sheet which is not originally intended for the culture room should be one which is capable of fusionbonding with the sheet for the culture room and has no adverse effect on culture. In the case of the second and third types of the culture bag, the medium storage room may be formed from one piece of the sheet for the storage room and one piece of a sheet which is not originally intended for the storage room. The sheet which is not originally intended for the culture room and the sheet which is not originally intended for the storage room may be produced from polyvinyl chloride, ethylene-vinyl acetate-carbon monoxide copolymer, or ethylene-vinyl acetate copolymer (containing 40-50 wt. % vinyl acetate), or a mixture thereof. These sheets should have a degree of gas permeability equal to or lower than that of the sheets for the culture room and storage room. In the case of the second and third types of the culture bags, the tube as the passage should preferably be provided with a stopper which can be opened at an appropriate time. This stopper should preferably be fusion-bonded to the tube.

The first, second, and third types of the culture bags may be modified such that the culture room is divided into upper and lower two compartments by a partition. The partition may be formed zigzag or aslant. The zigzag partition may have a gap at the lower corner through which cells can pass. The aslant partition consists of two parts, one extending aslant downward from the left side of the culture room and the other extending aslant downward from the right side of the culture room, which do not join each other. The partition may be curved.

The partition facilitates the separation of grown cells after static culture simply by suspending the culture bag, with the tubes upward. In the suspended culture bag the grown cells move downward along the aslant partition and enter the lower compartment of the room through the gap. After cell separation, the culture bag is turned upside down and the culture medium is discharged through the tube. The cell separation in this manner eliminates the necessity of using mechanical separation (such as centrifugation and filtration) which is liable to cause damage to the grown cells. Moreover, the cell separation in this manner makes it possible to continue cell culture without any fear of contamination simply by replenishing a new culture medium, because the grown cells remain in the bag.

The sheet for the culture room used to constitute the culture room of the first, second, and third types of the culture bag may be a three-layer laminate sheet, with the outer layers being made of a resin composition composed of 100 parts by weight of vinyl chloride homopolymer or copolymer and 150-260 parts by weight of ethylene-n-butyl acrylate-carbon monoxide copolymer, the core being made of ethylene-n-butyl acrylate-carbon monoxide copolymer. The outer layers of the laminated sheet should have a gas permeability of 600-3000 ml/m$^2$.24hr.atm to oxygen and a gas permeability of 1000-30,000 ml/m$^2$.24hr.atm to carbon dioxide. The outer layers give the laminated sheet high mechanical strength and good heat resistance. On the other hand, the core layer has good gas permeability. The thickness of the core layer should preferably be 150-300 $\mu$m. With a core thinner than 150 $\mu$m, the laminated sheet needs thicker outer layers, which lowers the gas permeability. With a core thicker than 300 $\mu$m, the laminated sheet is poor in heat resistance and mechanical strength and liable to wrinkling. The total thickness of the laminated sheet should preferably be 200-400 $\mu$m. The laminated sheet thicker than 400 $\mu$m is poor in clarity and flexibility. The laminated sheet thinner than 200 $\mu$m is poor in mechanical strength and liable to wrinkling. Basically, this laminated sheet may be prepared in the same manner as used for the above-mentioned sheet for the culture room.

The laminated sheet may be prepared by one of the following four methods. (a) Coating both sides of a core sheet with a solution of resin composition which forms a film after drying. Or, dry bonding of a core sheet with two sheets as the outer layers. (b) Thermolamination of a core sheet with two sheets as the outer layers. (c) Coating both sides of a core sheet with an extruded molten resin which forms the outer layers. (d) Lamination of a core sheet and outer layers by coextrusion.

The thus obtained laminated sheet is superior in gas permeability and free of plasticizer such as dioctyl phthalate. In addition, it is characterized by flexibility, high mechanical strength, and good fabricability such as fusion-bonding.

The invention will be described in more detail with reference to the following examples, which are not intended to restrict the scope of the invention.

REFERENTIAL EXAMPLE 1

An ethylene-n-butyl acrylate-carbon monoxide copolymer was prepared by vigorously stirring a mixture composed of 57 wt. % ethylene, 33 wt. % n-butyl acrylate, and 10 wt. % carbon monoxide, together with t-butyl peroxyisobutyrate, in a reactor at 180° C. and 27,000 psi. This copolymer has a melt flow rate of 12 g/10 min (as measured according to ASTM D1238).

REFERENTIAL EXAMPLE 2

An ethylene-vinyl acetate-carbon monoxide copolymer was prepared by vigorously stirring a mixture composed of 66 wt. % ethylene, 24 wt. % vinyl acetate, and 10 wt. % carbon monoxide, together with t-butyl peroxyisobutyrate, in a reactor at 179° C. and 27,000 psi. This copolymer has a melt flow rate of 35 g/10 min (as measured according to ASTM D1238).

EXAMPLE 1

A resin composition was prepared by melt-mixing at 180° C. using an extruder 100 parts by weight of vinyl chloride-ethylene copolymer (having an average degree of polymerization of 1300 and containing 4 wt. % ethylene), 160 parts by weight of ethylene-n-butyl acrylate-carbon monoxide copolymer (containing 57 wt. % ethylene, 33 wt. % n-butyl acrylate, and 10 wt. % carbon monoxide) prepared in Referential Example 1, 1.0 part by weight of Ca-Zn type stabilizer ("Mark 37" made by Adeka Argus Co., Ltd.), 15 parts by weight of epoxidized soybean oil ("O-130P" made by Adeka Argus Co., Ltd.), and 1 part by weight of polyethylene wax ("Hiwax 4202E" made by Mitsui Petrochemical Co., Ltd.). The resin composition was pelletized.

The pellets were formed into a sheet (0.15 mm thick) by extrusion at 180° C. through a 60-mm single-screw extruder equipped with a 400-mm wide T-die. The pellets were also formed into a tube (4 mm in inside diameter and 5 mm in outside diameter) by extrusion at 180° C. through the same extruder as above equipped with a tube die.

The thus obtained sheet (for the culture room) was cut into two approximate rectangles measuring 20 cm by 27 cm. The two rectangular sheets were placed one over the other, with three pieces of the tube held between them at one end thereof. The peripheries of the sheets were fusion-bonded, together with the tubes, by high-frequency sealing. Thus there was obtained a culture bag (1) consisting of a 200-ml culture room (2), a medium injection tube (3), a cell injection tube (4), and a sampling tube (5), as shown in FIG. 1.

EXAMPLES 2 TO 4

Culture bags were prepared in the same manner as in Example 1 except that the amount of ethylene-n-butyl acrylate-carbon monoxide copolymer in the resin composition was changed to 240 parts by weight (in Example 2), the sheet thickness was changed to 0.4 mm (in Example 3), and the amount of the copolymer in the resin composition was changed to 240 parts by weight and the sheet thickness was changed to 0.4 mm (in Example 4).

Tests for physical properties

The sheets used for culture bags in Examples 1 to 4 were tested for total light transmittance and permeability to oxygen and carbon dioxide. The results are shown in Table 1.

Experiment 1

The culture bags obtained in Examples 1 to 4 were used for experiments on cell culture in the following manner. First, the culture bag was sterilized with ethylene oxide. The culture room was filled with 200 ml of serum-free medium (made by Kyokuto Pharmaceutical Industrial Co., Ltd.) through the tube (3). Then, the culture medium was inoculated with as many cells as $5 \times 10^4$ cells/ml, which were injected through the tube (4). These operations were carried out in a clean bench. The cells are the hybridomas obtained by cell fusion between P3/NS1/1-Ag4-1 cells (ATCC No. TIB-18, referred to as "established cell line NS-1" hereinafter) and mouse spleen cells. With all the tubes closed by pinchcocks, the culture bag was placed in an incubator at 37° C. for five days for static culture in an atmosphere of 5% carbon dioxide. On the fifth day of culture, the culture medium was sampled through the tube (5) to count the number of cells.

For comparison, static culture was carried out for five days in a carbon dioxide incubator under the same conditions as mentioned above, using a 150-cm³ polystyrene culture flask (made by Iwaki Glass Co., Ltd.) containing 30 ml of serum-free medium and hybridomas ($5 \times 10^4$ cells/ml). During incubation, the stopper of the culture flask was kept slightly open. On the fifth day of culture, the number of cells was counted.

The results are shown in Table 1.

Experiment 2

Cell culture was carried out in the same manner as in Experiment 1, except that the culture medium (140 ml) was serum-free medium RPMI 1640 (purchased from Dainippon Pharmaceutical Co., Ltd.) incorporated with 10 vol % fetal calf serum under sterile conditions. The cells were NS-1 as many as $5 \times 10^4$ cells/ml. At the end of cell culture, the number of cells was counted.

For comparison, the same procedure as above was repeated using a culture flask as in Experiment 1 that employed 30 ml of culture medium. The cells were NS-1 as many as $5 \times 10^4$ cells/ml. At the end of cell culture, the number of cells was counted.

The results are shown in Table 1.

It is noted from Table 1 that the culture bags in Examples 1 to 4 are superior in gas permeability and clarity and they permit a high growth rate of cells.

TABLE 1

| Example No. | Copolymer (parts by weight) | Thickness of sheet (mm) | Total light transmittance (%) | Oxygen permeability (ml/m² · 24 hr · atm) | Carbon dioxide permeability (ml/m² · 24 hr · atm) | Cell count on 0th day (cells/ml) | Cell count on 5th day Experiment 1 | Cell count on 5th day Experiment 2 |
|---|---|---|---|---|---|---|---|---|
| 1 | 160 | 0.15 | 93.4 | 1,680 | 12,430 | $5 \times 10^4$ | $8.0 \times 10^5$ | $8.0 \times 10^5$ |
| 2 | 240 | 0.15 | 93.7 | 2,460 | 20,260 | $5 \times 10^4$ | $8.6 \times 10^5$ | — |
| 3 | 160 | 0.4 | 91.8 | 960 | 5,800 | $5 \times 10^4$ | $7.0 \times 10^5$ | — |
| 4 | 240 | 0.4 | 92.1 | 1,040 | 7,200 | $5 \times 10^4$ | $7.3 \times 10^5$ | — |

TABLE 1-continued

| Example No. | Copolymer (parts by weight) | Thickness of sheet (mm) | Total light transmittance (%) | Oxygen permeability (ml/m². 24 hr · atm) | Carbon dioxide permeability (ml/m². 24 hr · atm) | Cell count on 0th day (cells/ml) | Cell count on 5th day Experiment 1 | Cell count on 5th day Experiment 2 |
| --- | --- | --- | --- | --- | --- | --- | --- | --- |
| Culture flask | — | — | — | — | — | $5 \times 10^4$ | $6.5 \times 10^5$ | $7.0 \times 10^5$ |

EXAMPLE 5

A resin composition was prepared in the same manner as in Example 1 except that the ethylene-n-butyl acrylate-carbon monoxide copolymer was replaced by 100 parts by weight of ethylene-vinyl acetate-carbon monoxide copolymer (obtained in Referential Example 2) and the amount of epoxidized soybean oil was changed to 10 parts by weight. This resin composition was made into a 0.4-mm thick sheet for the storage room. This sheet was cut into two approximate rectangles. This sheet has an oxygen permeability of 170 ml/m².24hr.atm and a carbon dioxide permeability of 890 ml/m².24hr.atm. This sheet is the under-mentioned sheet (12) for the storage room.

The resin composition prepared in Example 1 was formed by extrusion into a 0.2-mm thick sheet for the culture room. This sheet was cut into approximate rectangles as mentioned above. This sheet has an oxygen permeability of 1420 ml/m².24hr.atm and a carbon dioxide permeability of 9210 ml/m².24hr.atm. This sheet is the undermentioned sheet (13) for the culture room.

Figure 2:
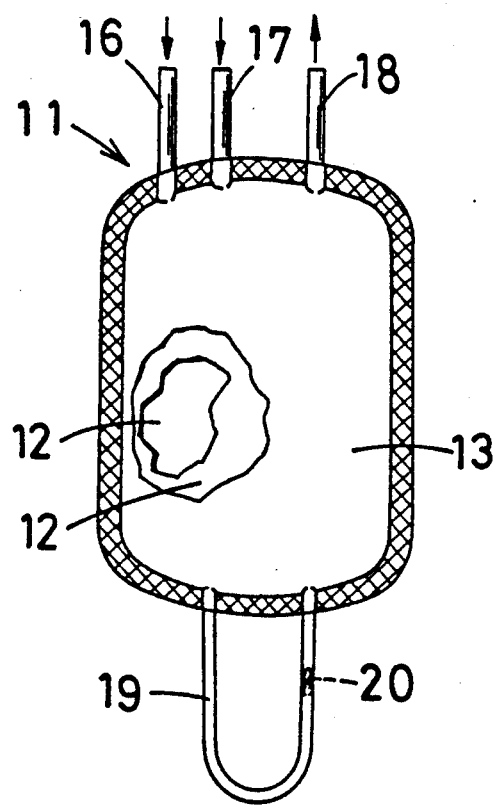
FIG. 2 is a partly cutaway plan view showing the culture bag in Example 5.
Figure 3:
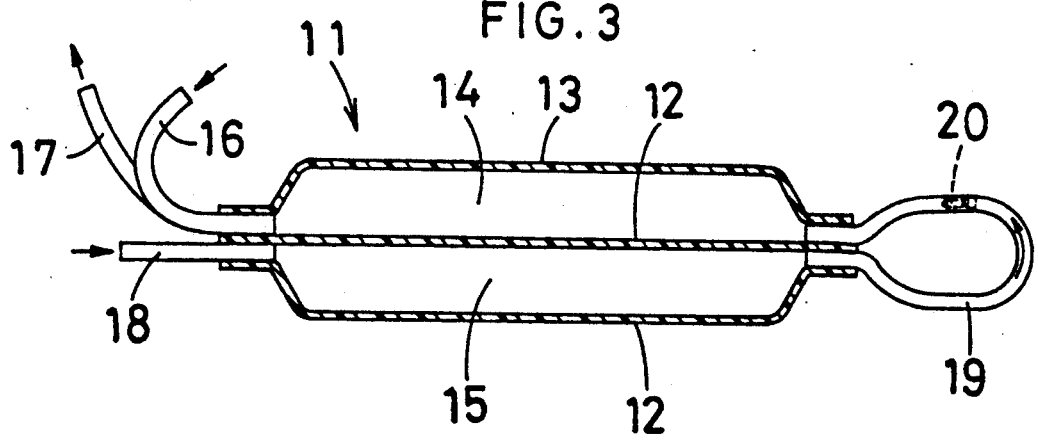
FIG. 3 is a longitudinal sectional view showing the culture bag in Example 5.

The thus obtained two kinds of sheets were formed into a culture bag which is constructed as schematically shown in FIGS. 2 and 3. The culture bag (11) is composed of the medium storage room (15) and the culture room (14). The medium storage room (15) is formed by two sheets (12 and 12) and the culture room is formed by one each of sheet (12) and sheet (13). These three sheets are joined together by fusion-bonding their peripheries. The culture room (14) is provided with the cell injection tube (16) and medium discharge tube (17), and the medium storage room is provided with the medium injection tube (18). The culture room is connected to the medium storage room by the connecting tube (19) through which the medium is transferred from the former to the latter.

Figure 4:
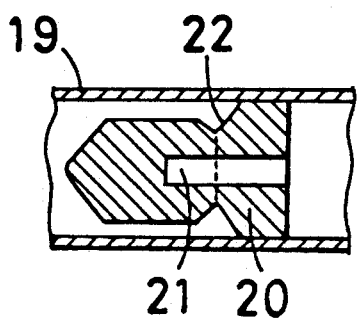
FIG. 4 is a sectional view showing the stopper which is not yet cut.
Figure 5:
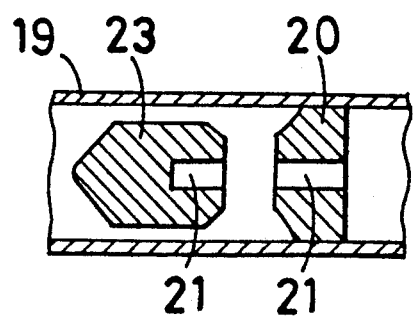
FIG. 5 is a sectional view showing the stopper which has been cut.

The connecting tube (19) is provided with the stopper (20) which prevents the medium-flow from the medium storage room (15) into the culture room (14) until it is required for culture. This stopper is fusion-bonded to the inside of the connecting tube (19). This stopper has the blind hole (21) and the narrow part (22) at its center, as shown in FIG. 4 and FIG. 5. For the medium to be transferred, the stopper (20) is broken at its narrow part (22) by bending the connecting tube so that the blind hole (21) becomes open, as shown in FIG. 5. The chip (23) formed by breaking the stopper (20) prevents the backflow of the medium.

The thus obtained culture bag is used in the following manner. First, the medium storage room (15) is filled with a culture medium through the medium injection tube (18), with the connecting tube (19) closed by the stopper (20). The culture medium is stored in the storage room (15) until it is used for culture. Then, the stopper (20) is broken to open the connecting tube (19), and the culture medium is transferred from the storage room (15) to the culture room (14). Immediately after that, cells are injected into the culture room (14) through the cell injection tube (16). The medium transfer may be accomplished by forcing a gas into the storage room (15) through the medium injection tube (18), or by suspending the culture bag (11), with the connecting tube (19) downward, so that the medium siphons from the storage room (15) into the culture room (14).

EXPERIMENT 3

The culture bag obtained in Example 5 was used for experiments on cell culture in the following manner. First, the culture room was filled with 140 ml of serum-free medium (RPMI 1640, the same one as used in Experiment 2) through the medium injection tube. With the medium injection tube closed by a pinchcock at its end, the culture bag was kept in an incubator of 5% carbon dioxide atmosphere at 37° C. for 16 hours. Then, the connecting tube was opened to transfer the culture medium into the culture room, and as many cells as $5 \times 10^4$ cells/ml were injected into the culture room through the cell injection tube. Cell culture was carried out under the same conditions as in Experiment 1, and the number of cells was counted on the fifth day of culture. It was found that the number of cells increased from $5 \times 10^4$ cells/ml to $7.8 \times 10^5$ cells/ml after culture for five days.

EXAMPLE 6

A resin composition was prepared in the same manner as in Example 1 except that the ethylene-n-butyl acrylate-carbon monoxide copolymer was replaced by 80 parts by weight of ethylene-vinyl acetate-carbon monoxide copolymer (obtained in Referential Example 2) and the amount of epoxidized soybean oil was changed to 10 parts by weight. This resin composition was made into a 0.35-mm thick sheet for the storage room. This sheet was cut into two approximate rectangles. This sheet has an oxygen permeability of 180 ml/m².24hr.atm and a carbon dioxide permeability of 780 ml/m².24hr.atm.

The resin composition prepared in Example 1 was formed by extrusion into a 0.15-mm thick sheet and a 0.3-mm thick sheet for the culture room. This sheet was cut into approximate rectangles as mentioned above. The 0.3-mm thick sheet has an oxygen permeability of 1080 ml/m².24hr.atm and a carbon dioxide permeability of 6810 ml/m².24hr.atm. This resin composition was formed into tubes.

The thus obtained sheets were formed into a culture bag which is constructed as schematically shown in FIG. 6. The culture room (39) is composed of the two kinds of sheets (32 and 33), which are placed one over the other, with their peripheries fusion-bonded by high-frequency sealing, together with the cell injection tube (36), the medium discharge tube (37), and the connecting tube (38) inserted at the ends of the culture room. The medium storage room (40) is composed of the two sheets (34 and 34), which are placed one over the other, with their peripheries fusion-bonded by high-frequency sealing, together with the medium injection tube (35) and the connecting tube (38) inserted at the ends of the medium storage room. Thus, the culture bag (31) is composed of the culture room (39), 200 ml in volume, and the medium storage room (40), 200 ml in volume, which are connected to each other through the connecting tube (38).

The connecting tube (38) is provided with the stopper (20) of the same structure as used in Example 5. Basically, the culture bag is used in the same manner as that in Example 5. The transfer of the culture medium into the culture room (39) can be accomplished by positioning the medium storage room (40) upside down or by pressing the medium storage room (40) with hands.

EXPERIMENT 4

The culture bag obtained in Example 6 was used for experiments on cell culture in the following manner. First, the culture room was filled with 140 ml of serum-free medium (RPMI 1640, the same one as used in Experiment 2) through the medium injection tube. With the medium injection tube closed by a pinchcock at its end, the culture bag was kept in an incubator of 5% carbon dioxide atmosphere at 37° C. for 16 hours. Then, the connecting tube was opened to transfer the culture medium into the culture room, and as many cells as $5 \times 10^4$ cells/ml were immediately injected into the culture room through the cell injection tube. Cell culture was carried out under the same conditions as in Experiment 1, and the number of cells was counted on the fourth day of culture. It was found that the number of cells increased from $5 \times 10^4$ cells/ml to $8.0 \times 10^5$ cells/ml after culture for four days.

EXAMPLE 7

Cell culture was carried out using the culture bag (41) as shown in FIG. 7. This culture bag is constructed in the same manner as that in Example 1, except that it has the zigzag partition (44). The zigzag partition has the gaps (45 and 46) at its lower corners, so that cells can pass through the gaps. The aslant parts of the partition function as the guide for cells.

A modified culture bag (51) is shown in FIG. 8. This culture bag has the partition (55) composed of two parts (52 and 53), one extending aslant downward from the left side and the other extending aslant downward from the right side, forming the gap (54) through which cells pass.

Another modified culture bag (61) is shown in FIG. 9. This culture bag has the partition composed of two parts (62 and 63), one extending aslant downward from the left side and the other extending aslant downward from the right side beyond the end of the first part, forming the gap (64) through which cells pass.

The partitions shown in FIGS. 7 to 9 are formed by partially fusion-bonding the two sheets (43 and 43) which form the culture room (42), so that the gaps are left unsealed.

The culture room (42) is provided with the medium injection tube (3), the cell injection tube (4), and the sampling tube (5) at its upper end.

The culture bags shown in FIGS. 7 to 9 permit grown cells to be introduced into the lower compartment of the bag through the gap of the partition, when it is suspended, with the tubes upward. Therefore, the culture bag permits the culture medium to be discharged when it is positioned upside down.

EXAMPLE 8

A three-layer laminated sheet (74) as shown in FIG. 10 was prepared from a core (71) and two outer layers (72 and 73) by thermolamination. The outer layers (0.05 mm thick) were prepared from a vinyl chloride type resin composition which has the same composition as in Example 1, except that the amount of the ethylene-n-butyl acrylate-carbon monoxide copolymer is 160 parts by weight and the amount of the epoxidized soybean oil is 10 parts by weight. The core (0.25 mm thick) was prepared from the same ethylene-n-butyl acrylate-carbon monoxide copolymer as mentioned above. This laminated sheet was cut into two rectangular sheets, which were then formed into the culture bag in the same manner as in Example 1.

EXAMPLE 9

The same procedure as in Example 8 was repeated except the following changes. The first outer layer (72), 0.08 mm thick, was prepared from a vinyl chloride type resin composition containing 80 parts by weight of ethylene-n-butyl acrylate-carbon monoxide copolymer. The second outer layer, 0.04 mm thick, was prepared from a vinyl chloride type resin composition containing 160 parts by weight of ethylene-n-butyl acrylate-carbon monoxide copolymer.

COMPARATIVE EXAMPLE 1

Culture bags were prepared in the same manner as in Example 1 except that the amount of ethylene-n-butyl acrylate-carbon monoxide copolymer in the resin composition was changed to 100 parts by weight and the sheet thickness was changed to 0.36 mm.

Tests for physical properties

The sheets used for culture bags in Examples 8 and 9 and Comparative Example 1 were tested for total light transmittance and permeability to oxygen and carbon dioxide. The results are shown in Table 2.

EXPERIMENT 5

The culture bags obtained in Examples 8 and 9 and Comparative Example 1 were used for experiments on cell culture in the same manner as in Experiment 1. The number of cells was counted on the fourth day of culture. The results are shown in Table 2.

It is noted from Table 2 that the culture bags used in Examples are superior in gas permeability and clarity and they permit a high growth rate of cells.

TABLE 2

| Exmaple No. | Thickness of sheet (mm) | Total light transmittance (%) | Oxygen permeability ($ml/m^2 \cdot 24\ hr \cdot atm$) | Carbon dioxide permeability ($ml/m^2 \cdot 24\ hr \cdot atm$) | Cell countr on 0th day (cell/ml) | Cell count on 4th day (cell/ml) |
|---|---|---|---|---|---|---|
| 8 | 0.35 | 92.6 | 2,200 | 12,000 | $5 \times 10^4$ | $9.0 \times 10^5$ |
| 9 | 0.37 | 92.1 | 1,400 | 7,000 | $5 \times 10^4$ | $8.8 \times 10^5$ |
| Comparative Example 1 | 0.36 | 93.8 | 500 | 3,500 | $5 \times 10^4$ | $5.8 \times 10^5$ |
| Culture | — | — | — | — | $5 \times 10^4$ | $6.3 \times 10^5$ |

TABLE 2-continued

| Exmaple No. | Thickness of sheet (mm) | Total light transmittance (%) | Oxygen permeability (ml/m² · 24 hr · atm) | Carbon dioxide permeability (ml/m² · 24 hr · atm) | Cell countr on 0th day (cell/ml) | Cell count on 4th day (cell/ml) |
|---|---|---|---|---|---|---|
| flask | | | | | | |

What is claimed is:

1. A culture bag which comprises a culture room formed by fusion-bonding a transparent sheet for the culture room and at least one opening formed therein, said sheet being made of a resin composition composed of 100 parts by weight of vinyl chloride homopolymer or copolymer and 150-260 parts by weight of ethylene-n-butyl acrylate-carbon monoxide copolymer, and having a gas permeability of 600-3000 ml/m².24hr.atm to oxygen and a gas permeability of 1000-30,000 ml/m².24hr.atm to carbon dioxide.

2. A culture bag as claimed in claim 1, wherein the culture room is formed by fusion-bonding the peripheries of two sheets, at least one of which being made of said resin composition.

3. A culture bag which comprises an integrally formed culture room and medium storage room, and at least one each of cell injection opening and medium discharge opening formed in the culture room and a medium injection opening formed in the medium storage room, with the culture room and medium storage room communicating with each other through a passage, said culture bag being formed by fusion-bonding the peripheries of two sheets for the storage room and one sheet for the culture room in such a manner that the two sheets for the storage room face to each other to form the medium storage room and one of the two sheets for the storage room and the one sheet for the culture room face to each other to form the culture room, said sheets for the storage room being made of a resin composition composed of 100 parts by weight of vinyl chloride homopolymer or copolymer and 30-150 parts by weight of ethylene-vinyl acetate-carbon monoxide copolymer, and having a gas permeability of 100-350 ml/m².24hr.atm to oxygen and a gas permeability of 200-1000 ml/m².24hr.atm to carbon dioxide, said sheet for the culture room being made of a resin composition composed of 100 parts by weight of vinyl chloride homopolymer or copolymer and 150-260 parts by weight of ethylene-n-butyl acrylate-carbon monoxide copolymer, and having a gas permeability of 600-3000 ml/m².24hr.atm to oxygen and a gas permeability of 1000-30,000 ml/m².24hr.atm to carbon dioxide.

4. A culture bag which comprises a culture room and a medium storage room communicating with each other through a passage connected to at least one opening formed in the culture room and at least one opening formed in the medium storage room, said culture room being formed by fusion-bonding a sheet for the culture room and said medium storage room being formed by fusion-bonding a sheet for the storage room, said sheet for the culture room being made of a resin composition composed of 100 parts by weight of vinyl chloride homopolymer or copolymer and 150-260 parts by weight of ethylene-n-butyl acrylate-carbon monoxide copolymer, and having a gas permeability of 600-3000 ml/m².24hr atm to oxygen and a gas permeability of 1000-30,000 ml/m².24hr.atm to carbon dioxide, said sheet for the storage room being made of a resin composition composed of 100 parts by weight of vinyl chloride homopolymer or copolymer and 30-150 parts by weight of ethylene-vinyl acetate-carbon monoxide copolymer, and having a gas permeability of 100-350 ml/m².24hr.atm to oxygen and a gas permeability of 200-1000 ml/m².24hr.atm to carbon dioxide.

5. A culture bag as claimed in claim 4, wherein the culture room is formed by fusion-bonding the peripheries of two sheets, at least one of which being made of said resin composition.

6. A culture bag as claimed in any one of claims 1 to 5, wherein the culture room is constructed such that two sheets constituting the culture room are partially fusion-bonded to form a partition which separates the culture room into upper and lower compartments, said partial fusion-bonding being accomplished in such a manner that at least one unsealed part forms a cell passage and the upper side of at least one of the sealed parts functions as the guide which leads cells to the unsealed part.

7. A culture bag as claimed in any one of claims 1 to 5, wherein the sheet for the culture room is a laminated sheet composed of two outer layers and a core, said outer layers being made of said resin composition of the sheet for the culture room, and said core being made of ethylene-n-butyl acrylate-carbon monoxide copolymer.

* * * * *